United States Patent
Buvat et al.

(10) Patent No.: US 10,673,076 B2
(45) Date of Patent: Jun. 2, 2020

(54) METHOD FOR PRODUCING PROTON-CONDUCTING PLATINUM PARTICLES WITH A LARGE ACTIVE SURFACE AREA AND SURFACE-GRAFTED WITH SPECIFIC, PROTON-CONDUCTING POLYMERS

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR)

(72) Inventors: Pierrick Buvat, Montbazon (FR); Janick Bigarré, Tours (FR); Christophe Coutanceau, Poitiers (FR); Stève Baranton, Poitiers (FR); Delphine Dru, Sorigny (FR)

(73) Assignee: COMMISSARIAT À L'ÉNERGIE ATOMOIQUE ET AUX ÉNERGIES ALTERNATIVES, Paris (FR)

( * ) Notice: Subject to any disclaimer, the term of this patent is extended or adjusted under 35 U.S.C. 154(b) by 76 days.

(21) Appl. No.: 16/089,240

(22) PCT Filed: Apr. 3, 2017

(86) PCT No.: PCT/EP2017/057879
§ 371 (c)(1),
(2) Date: Sep. 27, 2018

(87) PCT Pub. No.: WO2017/174524
PCT Pub. Date: Oct. 12, 2017

(65) Prior Publication Data
US 2019/0109329 A1    Apr. 11, 2019

(30) Foreign Application Priority Data

Apr. 4, 2016 (FR) .................. 16 52936

(51) Int. Cl.
| | |
|---|---|
| H01M 4/90 | (2006.01) |
| H01M 4/92 | (2006.01) |
| B01J 23/42 | (2006.01) |
| C08F 292/00 | (2006.01) |
| B01J 37/02 | (2006.01) |

(Continued)

(52) U.S. Cl.
CPC .......... *H01M 4/9008* (2013.01); *B01J 23/42* (2013.01); *B01J 37/009* (2013.01);
(Continued)

(58) Field of Classification Search
CPC .... H01M 4/9008; H01M 4/926; H01M 4/923; B01J 37/346; B01J 23/42; C08F 292/00
See application file for complete search history.

(56) References Cited

U.S. PATENT DOCUMENTS 9,421,531 B2 *  8/2016  Buvat ............... C08F 2/38
9,446,392 B2 *  9/2016  Buvat ............... C08F 12/30

FOREIGN PATENT DOCUMENTS

| FR | 2 982 173 A1 | 5/2013 |
| FR | 2 982 264 A1 | 5/2013 |
| WO | 2013/068319 A2 | 5/2013 |

OTHER PUBLICATIONS

International Search Report for International Application No. PCT/EP2017/057879, dated May 8, 2017.
(Continued)

*Primary Examiner* — Stewart A Fraser
(74) *Attorney, Agent, or Firm* — Pearne & Gordon LLP

(57) ABSTRACT

A specific method for preparing platinum particles grafted with proton-conducting polymers and use of these particles as catalysts for oxygen reduction.

17 Claims, 2 Drawing Sheets

(51) Int. Cl.
  *C08F 12/30* (2006.01)
  *B01J 37/34* (2006.01)
  *B01J 37/06* (2006.01)
  *B01J 37/00* (2006.01)
  *B01J 37/16* (2006.01)
  *C07C 323/52* (2006.01)
  *C08F 112/14* (2006.01)

(52) U.S. Cl.
  CPC ............ *B01J 37/0213* (2013.01); *B01J 37/06* (2013.01); *B01J 37/16* (2013.01); *B01J 37/343* (2013.01); *B01J 37/346* (2013.01); *C07C 323/52* (2013.01); *C08F 12/30* (2013.01); *C08F 112/14* (2013.01); *C08F 292/00* (2013.01); *H01M 4/923* (2013.01); *H01M 4/926* (2013.01); *C08F 2438/01* (2013.01)

(56) References Cited

OTHER PUBLICATIONS

Written Opinion for International Application No. PCT/EP2017/057879, dated May 8, 2017.

Preliminary French Search Report for Application No. 16 52936, dated.

Anne-Claire Ferrandez et al., "Chemical Functionalization of Carbon Supported Metal Nanoparticles by Ionic Conductive Polymer via the "Grafting From" Method", Chemistry of Materials, vol. 25, No. 19, Oct. 8, 2013, pp. 3797-3807.

Anne-Claire Ferrandez et al., "Pt Particles Functionalized on the Molecular Level as New Nanocomposite Materials for Electrocatalysis", Langmuir, vol. 28, No. 51, Dec. 21, 2012, pp. 17832-17840.

Delphine Dru et al., "Fluorine-Free Pt Nanocomposites for Three-Phase Interfaces in Fuel Cell Electrodes", ACS Catalysis, vol. 6, No. 10, Oct. 7, 2016, pp. 6993-7001.

Srinivasan Harish et al., "Microwave assisted polyol method for the preparation of Pt/C, Ru/C and PtRu/C nanoparticles and its application in electrooxidation of methanol", Journal of Power Sources, Elsevier SA, CH, vol. 214, Apr. 1, 2012, pp. 33-39.

Specification and drawings for U.S. Appl. No. 16/078,955, "Method for Preparing Proton-Conducting Particles Suitable for Catalysing Oxygen Reduction or Hydrogen Oxidation by Grafting Specific Proton-Conducting Polymers to the Surface of Same", filed Aug. 22, 2018.

* cited by examiner

METHOD FOR PRODUCING PROTON-CONDUCTING PLATINUM PARTICLES WITH A LARGE ACTIVE SURFACE AREA AND SURFACE-GRAFTED WITH SPECIFIC, PROTON-CONDUCTING POLYMERS

CROSS-REFERENCE TO RELATED APPLICATIONS

This is a National Stage application of PCT international application PCT/EP2017/057879, filed on Apr. 3, 2017, which claims the priority of French Patent Application No. 16 52936, filed Apr. 4, 2016, both of which are incorporated herein by reference in their entirety.

TECHNICAL FIELD

This invention relates to a method for preparing platinum particles with a large active surface area, these particles being, in addition, proton conducting thanks to a functionalisation of said particles with specific proton-conducting organic polymers.

These particles have for characteristics of having a catalytic activity (in particular, for the oxidation of hydrogen or the reduction of oxygen) while still having a proton conductivity.

Therefore, these particles have their application in the elaboration of electrode materials, in particular of materials intended to enter into the constitution of catalytic layers of electrodes for fuel cells, such as cells operating with $H_2$/air or with $H_2/O_2$ (known by the abbreviation PEMFC meaning "Proton Exchange Membrane Fuel Cell").

As such, this invention relates to the field of fuel cells operating on the principle of the oxidation of hydrogen and reduction of oxygen.

Prior Art

A fuel cell is an electrochemical generator, which converts the chemical energy into electrical energy thanks to two electrochemical reactions: an oxidation reaction at the anode of a fuel (hydrogen) combined with a reduction reaction at the cathode of an oxidiser (air or oxygen).

Conventionally, this type of fuel cells comprises a plurality of electrochemical cells mounted in series, with each cell comprising two electrodes with opposite polarity separated by a proton exchange membrane acting as a solid electrolyte, this membrane providing the passage to the cathode of the protons formed, by electrochemical reaction, during the oxidation of the fuel at the anode.

The aforementioned electrochemical reactions (oxidation and reduction) are produced at the level of specific zones of the electrodes (also referred to as active zones corresponding structurally to catalytic layers) which form the junction between the diffusion layer (at the level of which the supply with reagents occurs) of the electrodes and the membrane and require, in order to be produced, the use of catalysts, which consist, conventionally, for cells of the PEMFC type, of platinum particles.

In light of the costs involved by the presence of a catalyst such as platinum, it is suitable to obtain a maximum of catalytic surface area for a given mass of metal, with such an objective able to be achieved by platinum particles of nanometric sizes (also called platinum nanoparticles).

It is also suitable, so that the electrochemical reactions can take place, that the platinum particles be in contact with the fuel or oxidiser (according to whether on the anode or on the cathode), with the proton conductor constituting the membrane and with the electronic conductor entering into the constitution of the electrode (this electronic conductor being conventionally a carbon material), this contact zone being known under the name of triple point, the electrode will be all the more effective if the number of triple points is high.

In other terms, at these triple points, there is on the platinum particles:

a physical continuity with the electrolyte membrane, in order to provide a conduction of the protons $H^+$;
a physical continuity with the electronic conductor, in order to provide the conduction of the electrons; and
a physical continuity with the zone of diffusion of the electrodes, in order to provide for the diffusion of the gases (oxygen or hydrogen for PEMFC cells).

The maintaining over time of these triple points supposes compliance with the integrity of the contact zones between the various elements entering into the constitution of these triple points, which implies a maintaining of the physical integrity of these various elements, in particular of the platinum particles.

However certain studies have shown that it is possible to observe, during the operation of a cell, a degradation of the platinum particles (inducing, therefore, a decrease in the active surface area) either via dissolution phenomena or phenomena of the increase in particle sizes (stemming, conventionally, from agglomeration phenomena).

These dissolution phenomena can be produced with cells that operate at very low pH levels (for example, a pH less than 1) and with high operating potentials with the cathode (for example, a potential greater than 1 V in relation to RHE (RHE meaning reversible hydrogen electrode)) the dissolved platinum able to be either in the water formed during the operation of the cell or inside the electrolyte membrane, generally, polymeric, which leads, within, to the formation of inactive platinum nanocrystals.

With regards to the phenomena concerning increase, they can occur with cells of which the platinum nanoparticles have a substantial mobility on the surface of the generally carbon support, whereon they are deposited, with this mobility depending on the surface energy of the latter.

In order to overcome these phenomena, high rate of platinum particles can be used with the disadvantages that this represents in terms of production costs, with regards to the very high price for platinum in the markets.

In order to decrease the loading rate while still accessing an effective active surface area, the studies concerned the optimisation of the electrode (here, comprising platinum particles)-membrane assemblies.

As such, it has been proposed to juxtapose, by intimate contact, the various elements (platinum particles, electrical conductor and electrolyte) required for the creation of triple points, this juxtaposition able to consist:

in mixing platinum particles with carbon powder (fulfilling the role of electrical conductor) and in impregnating the whole with electrolyte, in such a way as to guarantee a better contact with the membrane;
in depositing via technique of thin layer deposition (such as electrodeposition or physical spraying) of platinum particles, which makes it possible to deposit platinum according to low concentrations while still retaining a very high catalytic activity.

However, the units resulting from these techniques are fragile due to the low bonds involved to juxtapose the elements that comprise these units, which does not make it possible to prevent the phenomena of degradation due to the migration of the platinum particles which cause, therefore, a decrease in the life of these units.

In order to overcome these disadvantages, the authors of this invention have proposed, in WO 2013/068319, a method for preparing catalyst particles, more specifically, made of platinum, grafted, covalently, by proton-conducting polymers via an organic radical of an organic compound that is an initiator of a polymerisation of the ATRP type, of specific grafts described in this document, being grafts having the following formula (I'):

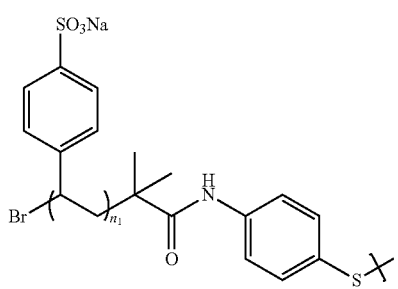

wherein $n_1$ corresponds to the repetition number of the repeating unit taken in parentheses and the brace indicating the location where said grafts are covalently bonded to the particles.

Starting with this method, the authors of this invention set the objective to further improve the aforementioned method and to propose a new method that would make it possible, furthermore, to obtain particles that, once incorporated, in a fuel cell, would make it possible to obtain an improvement in the electrochemical properties of the fuel cell, and more specifically, that would make it possible to obtain a good active surface area, without the latter be lessened by the grafting of proton-conducting polymers.

Also, the authors of this invention discovered that by using a specific ATRP initiator in the framework of the method of the invention as well as a specific method of synthesising of the particles before grafting, it is as such possible to obtain particles that have the aforementioned properties.

Disclosure of the Invention

As such, the invention relates to a method for preparing platinum particles bonded to a carbon material, said particles being grafted with grafts consisting of at least one polymer comprising at least one styrene repeating unit having at least one proton-conducting group, said method comprising:

a) a step of preparing said platinum particles bonded to a carbon material comprising an operation of heating under microwaves of a mixture comprising a platinum salt, said carbon material and at least one polyol compound, subject to which said particles are obtained;

b) a step of preparing at least one ethylene polymer by ATRP polymerisation of an ethylene monomer with an ATRP initiator having the following formula (I):

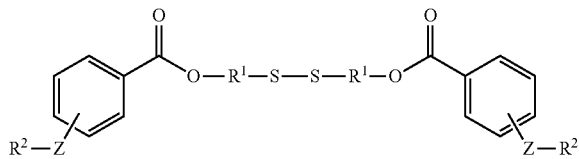

wherein:
the $R^1$ groups represent, independently of one another, an organic spacer group;
the Z groups represent, independently of one another, a single bond or an organic spacer group;
the $R^2$ groups represent, independently of one another, a halogen atom;
the resulting polymer having the following formula (II):

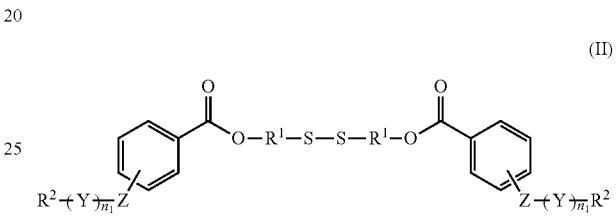

wherein Y corresponds to the styrene repeating unit having at least one proton-conducting group and $n_1$ to the repetition number of the repeating unit taken in parentheses, the $R^1$, $R^2$ and Z being such as defined hereinabove;

c) a step of contacting particles obtained in a) with the polymer obtained in b), subject to which particles are obtained grafted with grafts having the following formula (III):

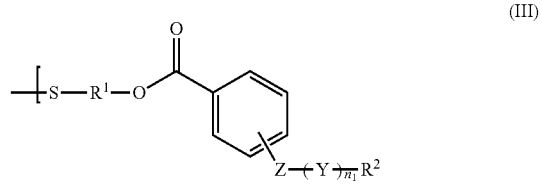

the brace indicating the location where the grafts are bonded, covalently, to the particles and the Fe, $R^2$, Z, Y and $n_1$ being such as defined hereinabove.

In particular, the $R^1$ groups can be identical to each other, in the same way as the Z groups can be identical to each other and the $R^2$ groups can be identical to each other.

Before going into any further detail in this description, we specify the following definitions.

The term polymer means, conventionally, in terms of the invention, a compound comprised by the chaining together of one or several repeating units.

The terms repeating unit means, conventionally, in terms of the invention, a bivalent organic group (i.e. a bridging group) coming from a monomer after polymerisation of the latter.

The term polymerisation of the ATRP type means an atom transfer radical polymerisation (ATRP). The mechanism of this type of polymerisation will be explained in more detail hereinbelow.

As such, thanks to the implementation of the method of the invention, it is as such possible to obtain platinum particles grafted by covalence via a remainder of the ATRP initiator compound with proton-conducting polymers, which makes it possible, when these particles are intended to enter into the constitution of electrodes (in particular on the catalytic layers of the latter) to provide good physical continuity with the adjacent electrolyte, when the latter also has a proton-conducting polymer base.

What is more, thanks to the specific choice of ATRP initiator, it was possible to obtain particles, which confer, to the cells, wherein they are incorporated, improved properties.

Finally, thanks to the association of the method of synthesis of the step a) and of the use of the aforementioned specific ATRP initiator, the particles obtained by the method of the invention have a large active surface area and, at the least, a retaining of the latter, after grafting of the particles obtained in the step a) and even an improvement in the active surface area after grafting.

In other terms, the authors of this invention were able to develop a method for synthesising platinum particles grafted with proton-conducting polymers, of which the active surface area is compounded, despite the screening phenomenon of the surface that is normally inherent to the grafting of these polymers. Also, thanks to the synergy obtained by the implementation of the means of the method of the invention, the grafting of these polymers makes it possible to render accessible catalytic zones that are not so for particles that are not grafted.

As mentioned hereinabove, the method of the invention comprises, firstly, a step a) of preparing said platinum particles bonded to a carbon material comprising an operation of heating under microwaves of a mixture comprising a platinum salt, said carbon material and at least one polyol compound, subject to which said particles are obtained.

The platinum salt can be a platinum halide salt, optionally hydrated, such as $H_2PtCl_6 \cdot 6H_2O$.

The carbon material (able to be equated with a carbon support) can be graphite, carbon black, carbon fibres, carbon tubes (such as carbon nanotubes) or graphene and, more specifically, carbon black.

The polyol compound, as its name indicated, is a compound comprising at least two —OH groups. It can be, in particular, a hydrocarbon compound comprising at least two carbon atoms each having at least one —OH group, with the compounds corresponding to this definition able to be ethylene glycol or glycerol.

From a practical standpoint, the polyol compound allows for the reduction in platinum salt in platinum with a zero oxidation state (i.e., in other terms, in metallic platinum).

Without being bound to theory, if we take as an example a polyol compound, ethylene glycol, the latter ensures, in a first step, the role of a solvent. Once the platinum salt is in solution, intermediate compounds are created, such as hydroxide and/or oxide compounds. Then, the dehydration, simultaneously with the heating, of ethylene glycol into acetaldehyde allows for the reduction of the metallic ions. This gentle reduction allows for a slow growth of the particles, the stopping of the growth of the latter resulting from a combination between the adsorption of by-products from the reaction on the metallic platinum (such as glycolates) and of the depletion of the medium in species to be reduced (here, the platinum salt). The glycolates can also ensure the role of surfactant that will preferably be adsorbed on certain parts of the platinum particles, which contributes to the creation of a relatively substantial number of extended domains on the surface of the particles.

Advantageously, this step a) can be carried out with a basic pH, i.e. with a pH greater than 7, such as a pH of 11, this pH contributing favourably to the decomposition of the salt and the formation of species, such as glycolate, when the polyol compound is ethylene glycol.

Advantageously, this step a) is carried out under an inert atmosphere, for example, a nitrogen atmosphere.

The heating under microwaves can be carried out by means of a microwave oven, for example, of the MARSXpress type from CEM®.

The heating can unfold by a rise in temperature going from the ambient temperature (for example, 20° C.) to a setpoint temperature (for example 100° C.) at atmospheric pressure and a power of at least 1,600 W followed by the maintaining of the setpoint temperature at this same power until the particles are obtained (for example, a duration of 5 minutes).

At the end of this step a), the pH of the mixture obtained is, advantageously, brought to an acidic pH, by the adding of an acid solution, such as a solution of hydrochloric acid.

At the end of this step a), after the optional step of adding of an acidic solution, the particles obtained are isolated, for example, via filtration (such as ultrafiltration), optionally rinsed then dried, in such a way as to remove the traces of water and solvent.

Before the operation of heating as such, it is possible to proceed with preparing the mixture comprising a platinum salt, a carbon material and at least one polyol compound, this preparation able to consist in contacting these various ingredients and in mixing them, for example, under ultrasounds, in order to obtain, in particular, a good dispersion of the carbon material.

Then, the method of the invention comprises a step b) of preparing at least one styrene polymer by ATRP polymerisation of a styrene monomer with an ATRP initiator having the aforementioned formula (I).

This step of preparation is governed by the mechanisms of the ATRP polymerisation, which operate on the principle of the reversible and fast formation of species referred to as "dormant species" by the creation of a covalent bond with a reactive radical species.

The initiator compound of a polymerisation of the ATRP type having formula (I) is a compound comprising at least one group able to initiate the ATRP polymerisation, i.e. a group able to cleave on a bond in order to form a first reactive species and a second reactive species, the first reactive species reacting later, with a first carbon having a double bond belonging to the monomer, the second reactive species being fixed to a second atom opposite the first carbon having the double bond.

In other terms, this mechanism can be summarised according to the following reaction scheme:

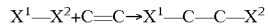

$X^1$-$X^2$ corresponding to the abovementioned initiator with $X^1$ corresponding to the first species and $X^2$ corresponding to the second species, the species $X^1$—C—C—$X^2$ being a dormant species, which can grow by successive additions of monomers of free radicals, as in a conventional radical polymerisation, the free radicals being created by removing of the $X^2$ group, which then is fixed after insertion of the monomer at the end of the polymer chain, which always constitutes a dormant species which can continue to grow when monomers subsist in the polymerisation medium.

For reasons of simplicity, we have shown hereinabove only the double bond of the monomer.

Furthermore, the initiator compound having formula (I) used in the scope of this step of preparing comprises at least one group capable of being grafted onto the surface of the aforementioned particles, i.e. a group able to react with the surface of said particles in order to form a covalent bond, whereby there subsists a radical of this initiator bonded covalently on the surface of said particles.

For the initiator compounds having formula (I), the group able to initiate a polymerisation of the ATRP type is the —Z—$R^2$ group mentioned hereinabove, this group being able to cleave, homolytically, on the carbon-halogen bond in order to form two reactive species, a first reactive carbon species (that can be symbolised by —C) and a second reactive species consisting of a halogen radical (that can be symbolised by $R_2$), the first species reacting with an end of the double bond of the monomer and the second species reacting with the opposite end of the double bond. In the formula (I), this —Z—$R^2$ group being represented as intersecting a carbon-carbon bond of the phenyl group, this means that it can be bonded to any of the carbon atoms of this phenyl group.

The group able to be grafted on the surface of particles corresponds, for this type of compounds, to the disulphide group —S—S—.

For the compounds having formula (I), the $R^1$ groups and the Z groups can represent, independently of one another, an alkylene group, for example, an ethylene group, a methylene group.

More specifically, the $R^1$ can be an ethylene group and the Z can be a methylene group.

When the Z represent a single bond, this means, in other terms, that $R^2$ is directly linked to any of the carbon atoms of the phenyl group.

For the compounds having formula (I), the —Z—$R^2$ groups can be located in para position with respect to the —COO— groups.

A particular ATRP initiator compound entering into the category of the compounds having formula (I) is a compound having the following formula (IV):

(IV)

The compounds having formula (I) can be synthesised by a nucleophilic substitution reaction between an acyl halide compound and an alcoholic compound, this reaction being based on the formation of an alcoholate from the deprotonation of the alcoholic compound in a basic medium (for example, in the presence, of triethylamine), the alcoholate formed as such reacting on the acyl chloride in order to form the initiator compound, generally at a temperature of about 0° C., in such a way as to ensure the stability of the alcoholate.

By way of example, when this entails preparing a compound having the aforementioned formula (IV), the acylation reaction can take place between the 2-hydroxyethyl-disulphide compound and the 4-chloromethylbenzoyl chloride compound according to the following reaction scheme:

this reaction being able to be carried out with chloroform as an organic solvent.

The monomers that can be used in the framework of the step of polymerisation are styrene monomers and can be, more specifically, monomers that have the following formula (V):

(V)

wherein:
$Z^1$ corresponds to a phenylene group; and
E corresponds to a proton-conducting group, optionally in the form of a salt, such as a sulphonic acid group, a phosphonic acid group or a carboxylic acid group.

A specific monomer having the meaning given hereinabove is a styrenesulfonic acid monomer, for example in the form of a salt, such as a sodium salt (in which case, sodium styrene sulphonate monomer can be mentioned).

An example of this type of monomer is a monomer having the following formula (VI):

(VI)

wherein $R^3$ is a hydrogen atom or a cation (for example, a metal alkaline cation).

In addition to the presence of one or several monomers such as defined hereinabove, the step of polymerisation unfolds, conventionally, in the presence of a metallic salt (for example, a metal halide, such as a copper halide, such as copper chloride) and of an organic ligand.

It is specified that the term organic ligand means an organic compound comprising at least one free doublet able to fill in an electronic gap of a metallic element (here, in our case, an electronic gap on the metallic element of the abovementioned salt) in order to form a metal complex.

By way of example, a suitable organic ligand can be a compound belonging to the family of pyridine compounds, such as bipyridine.

The step of polymerisation can be carried out, furthermore, in a water/organic solvent mixture (for example, an alcoholic solvent) under the flow on an inert gas (such as a flow of argon) during a temperature and duration that are suitable for generating the polymerisation.

Furthermore, this step of polymerisation can be followed by a step of hydrolysis intended to protonate the proton-conducting groups, when they have the form of a salt (i.e., in other terms, this step consists in replacing the cations of the salt with atoms of hydrogen).

The average molecular weights of the polymers obtained at the end of the step of polymerisation can range from 3,000 to 1,000,000 g/mol and more specifically from 80,000 to 700,000 g/mol and, more specifically, from 300,000 to 600,000 g/mol.

After the step b), the method of the invention comprises a step c) of contacting particles obtained in a) with the polymer obtained in b), subject to which particles are obtained grafted with grafts having the following formula (III):

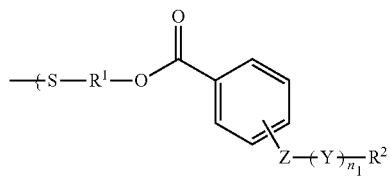

(III)

the $-Z-(Y)_{n_1}-R^2$ group, which intersects a carbon-carbon bond of the phenyl group, meaning that it can be bonded to any of the carbon atoms of the phenyl group.

This step c) of contacting can include an operation of dispersing the abovementioned particles, for example, in an electrophilic solvent (such as an amine solvent, such as hexylamine) followed by an operation of contacting the dispersion obtained with one or several polymers such as defined hereinabove in conditions that are sufficient to allow for the grafting by covalence of the polymers prepared in b).

Without being bound to theory, the polymer, in the presence of particles, will separate into two organic radicals by homolytic cleaving of the bond between the two sulphur atoms, the two radicals consisting of reactive species comprising free electrons located on sulphur atoms, these free electrons each associated with an electron present on the surface of the particles in order to form a covalent bond between the abovementioned radicals and the particles via the sulphur atoms, the resulting product being able to be diagrammed in the following way:

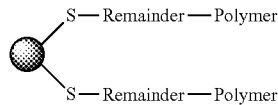

the solid sphere corresponding to a particle, —S-Remainder-corresponding to a radical of the ATRP initiator compound forming a bridge between the particle and the polymer (respectively, a first polymer chain and a second polymer chain).

With regards to the polymer, the proton-conducting group can be a sulphonic acid group —SO$_3$H, a carboxylic acid group —CO$_2$H or a phosphonic acid group —PO$_3$H$_2$, these groups being able to be present optionally in the form of salts.

At the end of the method of the invention, the grafting rate of polymer(s) (expressed as a percentage by weight of polymer in the particles) can range from 0.01 to 30% by weight and, more specifically ranging from 0.5 to 15% by weight and, more specifically again, ranging from 1 to 5% by weight, with this latter range being ideally associated with polymers having an average molecular weight ranging from 300,000 to 600,000 g/mol.

The particles being able to be obtained by the method of the invention, are platinum particles bonded to a carbon material (for example, covalently), said particles being grafted with grafts having the following formula (III):

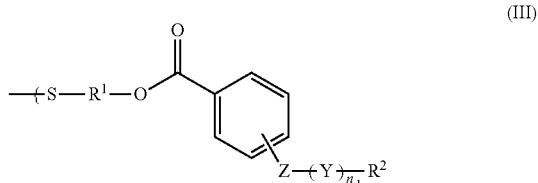

(III)

wherein the $R^1$, $R^2$, Z, Y and $n_1$ have the same definitions as those given hereinabove, the $-Z-(Y)_{n_1}-R^2$ group, which intersects a carbon-carbon bond of the phenyl group meaning that it can be bonded to any of the carbon atoms of the phenyl group.

With regards to the carbon material, it can be graphite, carbon black, carbon fibres, carbon tubes (such as carbon nanotubes), graphene.

The weight ratio between carbon material and platinum can be between 80/20 and 20/80, ideally between 45/55 and 65/35.

More specifically, $R^1$ and Z represent an alkylene group and $R^2$ a halogen atom, such as chlorine, while Y can represent a repeating unit coming from the polymerisation of a styrene monomer having the abovementioned formula (V) or (VI), such as a sodium styrene sulphonate monomer. The $-Z-(Y)_{n_1}-R^2$ group can also be in para position in relation to —CO—O— group.

For information, the brace indicates the location where the grafts are bonded, covalently, to the particles, themselves being bonded to a carbon material.

Specific particles in accordance with the invention can be platinum particles grafted by grafts having the following formula (VII):

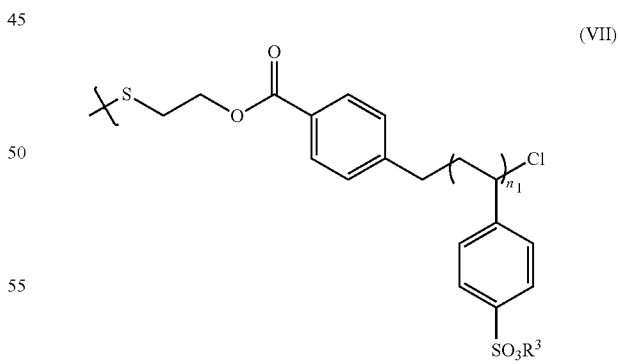

(VII)

with $R^3$ and $n_1$ being such as defined hereinabove.

Such particles are particularly interesting, because they make it possible to transpose the phenomenology of the triple point to the molecular scale, the role of the catalyst being fulfilled by the material that comprises the particle as such, the role of the proton conductor being fulfilled by the abovementioned polymers and the role of the electronic conductor being fulfilled by the carbon material. The covalent bonds between the electronic conductor and the catalyst on the one hand and between the proton-conducting material and the catalyst on the other hand provide, firstly, a better transfer of the charges (respectively, electrons and protons) and therefore better performance and, secondly, perfect stability in operating conditions as a cell, when these particles are used in cells. These two results make it possible to reduce the loading rate in catalyst for increased performance.

The particles of the invention are able to catalyse the reduction of oxygen or the oxidation of the hydrogen and have, all the more so, a substantial active surface area.

The particles of the invention can enter, therefore very naturally, into the constitution of electrodes of fuel cells, in particular fuel cells of the PEMFC type, more particularly in catalytic layers of electrodes of fuel cells.

As such, the invention also relates to electrodes that comprise such particles and fuel cells comprising at least one electrode-membrane-electrode assembly, wherein at least one of its electrodes is an electrode in accordance with the invention.

These particles do not show any sign of degradation below 220° C. (this limit being determined by TGA). Moreover, the electrochemical strength of the organic crown (formed by the polymers grafted to the particles) was demonstrated in a range of potentials from 0 to 1.2 V vs. RHE (RHE meaning reversible hydrogen electrode), which makes it possible to consider using these particles as catalysts for fuel cells of the PEMFC type.

These particles can be dispersed in an alcoholic solution. It is then possible to mix them with a proton-conducting ionomer in proportions ranging from 100/0 to 70/30. The solution can then be deposited on any type of carbon porous support (fabric or felt), the resulting product able to be used as an electrode of a fuel cell.

What is more, the particles of the invention, once incorporated into fuel cells, make it possible to obtain an improvement in the properties, such as the open circuit voltage, better activation of the electrochemical reactions within the cell, a less substantial ohmic drop and better power output, in relation to similar fuel cells, wherein however the particles introduced are particles grafted by grafts having formula (I').

Moreover, these particles have an electrocatalytic activity even when they are implemented without an ionomer of the Nafion type. This particularly remarkable result makes it possible to produce electrodes without Nafion. Associated with membranes alternative to Nafion, these particles will make it possible to produce membrane/electrode assemblies free of any Nafion.

As such, fuel cells, for example of the PEMFC type, include, conventionally, at least one electrode-membrane-electrode assembly, wherein at least one of its electrodes has a base of particles in accordance with the invention.

The membrane can have a proton-conducting polymer material base, with the polymer or polymers comprising this material being able to be of the same nature as the polymer or polymers grafted on the surface of said particles.

The invention shall now be described, with respect to the following non-limiting examples provided for the purposes of information.

BRIEF DESCRIPTION OF THE FIGURES

The FIG. 1 shows polarisation curves representing the change in the voltage E (in V) according to the current density D (in A/cm$^2$) for the Cell 1 (curve a') and the Cell 2 (curve b') of the example 5 and of the power curves representing the change in the power density P (in kW/cm$^2$) according to the current density D (in A/cm$^2$) (respectively curve a) and b) for the Cells 1 and 2).

The FIG. 2 shows polarisation curves representing the change in the voltage E (in V) according to the current density D (in A/cm$^2$) (respectively curves a'), b'), c') and d') for cells comprising particles of tests 2, 3, 4 and 7) and the power curves representing the change in the power density P (in kW/cm$^2$) according to the current density D (in A/cm$^2$) (respectively curves a), b), c) and d) for cells comprising particles of tests 2, 3, 4 and 7).

Figure 3:
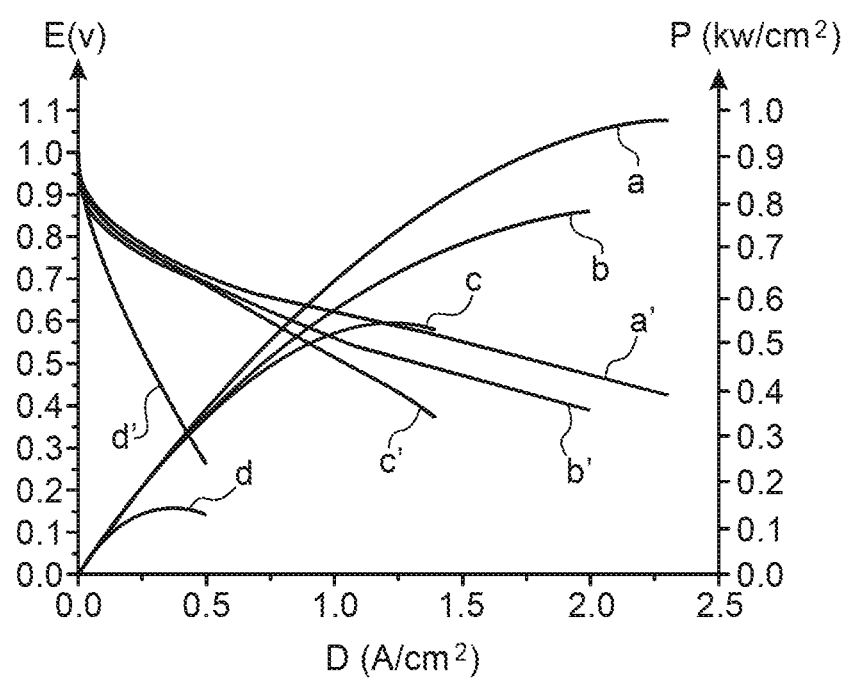

The FIG. 3 shows polarisation curves representing the change in the voltage E (in V) according to the current density D (in A/cm$^2$) (respectively curves a'), b'), c') and d') for cells comprising particles of tests 6, 7, 8 and 9) and the power curves representing the change in the power density P (in kW/cm$^2$) according to the current density D (in A/cm$^2$) (respectively curves a), b), c) and d) for cells comprising particles of tests 6, 7, 8 and 9).

DETAILED DESCRIPTION OF PARTICULAR EMBODIMENTS

Example 1

This example shows the preparation of an ATRP initiator in accordance with the invention: disulfanediyldiethane-2,1-diyl bis[4-(chloromethyl)benzoate] having the following formula (IV):

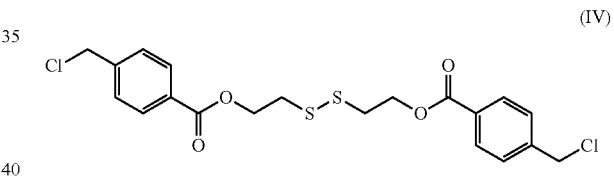

(IV)

To do this, in a 100 mL bicol are introduced, under an inert atmosphere, 2-hydroxyethyldisulphide (1.53 g; 9.9 mmol; 1 eq.), chloroform (30 mL) and triethylamine (4.22 g; 41.7 mmol; 4.2 eq.). The bicol is sealed under argon then immersed into an ice bath at 0° C.

Then, 4-chloromethylbenzoyl chloride (2.06 g; 10.9 mmol; 1.1 eq.) is introduced drop-by-drop. Then the mixture is allowed to return to ambient temperature for one night. The resulting reaction mixture is washed 4 times (an acid wash, a neutral wash, a basic wash then a neutral wash). The organic phases are gathered together and dried. The organic solvent is then removed in the rotary evaporator. The solid product obtained is then dried in the oven at 60° C. for one night.

The resulting product (with an output of 97%) corresponds to the product expected having the formula hereinabove according to the $^1$H NMR spectroscopy and elemental analysis, of which the results are provided hereinbelow.

$^1$H NMR (400 MHz, CDCl$_3$. δ=7.26 ppm): 8.5 (s, 1H, NH); 7.5-7.4 (m, 4H, H aromatic); 2.0 (s, 6H, CH$_3$)

$^{13}$C NMR (100 MHz, CDCl$_3$, δ=77.0 ppm): 170 (s, C=O); 137.2 (s, C$_q$—S); 132.8 (s, C$_q$—NH); 130.1 (d, HN—C$_q$—$\underline{C_H}$—$\underline{C_H}$—S); 120.5 (d, HN—, C$_q$—$\underline{C_H}$—$\underline{C_H}$—S); 63.0 (s, Br—$\underline{C}$(CH$_3$)$_2$); 32.5 (q, CH$_3$)

Elemental analysis (in %): (C$_{20}$H$_{20}$Cl$_2$O$_4$S$_2$), C: 52.1; H: 4.4; Cl: 15.5; O: 14; S: 14.

Example 2

This example shows the preparation of a polymer that can be diagrammed by the following formula hereinbelow:

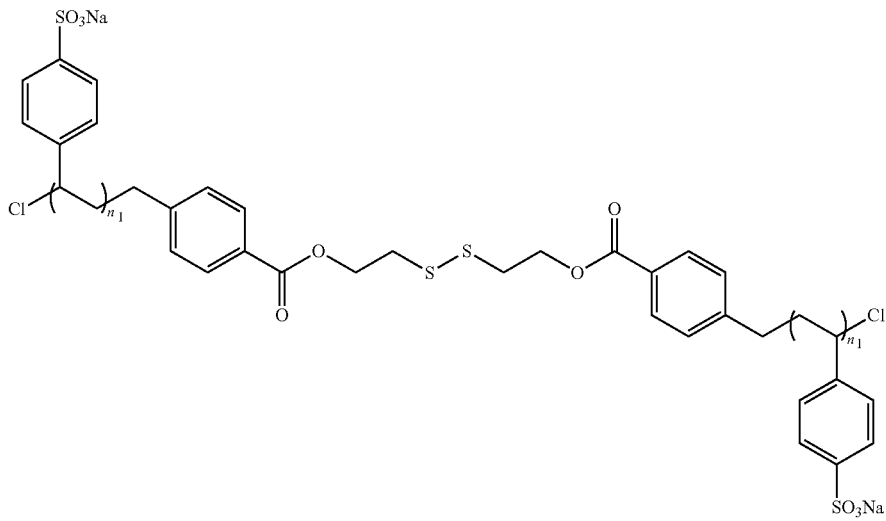

with $n_1$ corresponding to the repetition number of the unit taken in parentheses.

Various tests were implemented with different quantities of monomers (X).

To do this, in a first time, a 100 mL bicol is subjected to a thermal treatment under vacuum comprising 3 cycles with a heating phase and a cooling phase at ambient temperature.

The MilliQ water (48 mL) is introduced into the bicol and is degassed under vacuum by bubbling argon (15 minutes). Sodium styrenesulfonate (X g; Y mol; Z eq.) is then introduced under a flow of argon and argon is again bubbled in a vacuum.

In parallel, methanol (16 mL) is degassed under vacuum by bubbling argon (15 minutes) in a 25 mL pear-shaped flask. The initiator prepared in example 1 (50 mg; 0.09 mmol; 1 eq.) is then introduced under a flow of argon.

When the monomer is perfectly dissolved in the water, bipyridine (116 mg; 0.74 mmol; 8 eq.) and copper chloride (37 mg; 0.37 mmol; 4 eq.) are introduced under a flow of argon.

Argon is set to bubble in the system while drawing under vacuum.

The solution of initiator in the methanol is introduced with a syringe (20 mL) ensuring that the latter is conditioned under argon. Three vacuum-argon cycles are finally carried out.

The bicol is finally set in place in an oil bath heated beforehand to 45° C. After approximately 21 hours of polymerisation, the reaction is stopped by venting the system. The solution changes from a brown colour to a green-blue colour.

The reaction mixture is then filtered over silica gel, in order to remove the chloride ions contained in the catalytic system and trapped in the polymer.

The filtrate is then concentrated under vacuum, in order to increase the concentration in polymer and therefore facilitate precipitation.

Finally, the polymer is precipitated in cold methanol.

The polymer obtained is a tacky white solid then is placed in the oven at 65° C. for 1 night.

The resulting polymer corresponds to the product expected having the formula hereinabove according to the $^1$H NMR analyses, of which the results are provided hereinbelow.

$^1$H NMR (D$_2$O) δ: 7.5 (s large, aromatic proton), 6.6 (s large, aromatic proton), 1.4 (s large, methyl proton).

The quantities of monomers used are summarised in the following table:

| Degree of polymerisation sought (DP) | Monomer weight (g) X | Number of moles Y (in moles) | Number of equivalents Z |
|---|---|---|---|
| 500 | 9.4 | 0.045 | 500 |
| 1,000 | 18.8 | 0.09 | 1,000 |
| 1,500 | 28.2 | 0.135 | 1,500 |
| 2,000 | 37.6 | 0.18 | 2,000 |
| 2,500 | 47 | 0.225 | 2,500 |

The characteristics of the polymers obtained for each one of the tests are listed in the following table.

| Degree of polymerisation sought (DP) | Molar weight of the polymer obtained (in g) | Degree of experimental polymerisation |
|---|---|---|
| 500 | 76,000 | 370 |
| 1,000 | 140,000 | 680 |
| 1,500 | 222,000 | 1,080 |
| 2,000 | 300,000 | 1,460 |
| 2,500 | 359,000 | 1,740 |

Example 3

This example shows the preparation of platinum particles bonded to a carbon material of the carbon black type (denoted, in the formula hereinbelow "Vulcan XC72"), represented by the formula hereinbelow:

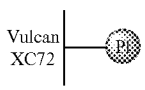

according to two methods:
- a method that is not in accordance with the invention involving a microemulsion referred to as "water-in-oil" (referred to as method 3a); and
- a method in accordance with the invention involving a polyol medium and a heating by microwave radiation (referred to as method 3b).

a) Synthesis of the Particles Via Microemulsion Referred to as "Water-in-Oil"

Heptane (37.4 g) and Brij® 30 (8.6 g) are poured into a reactor. The reactor is then manually stirred and immediately vigorously, in order to prevent the precipitation of the Brij® 30, until the mixture is translucent.

In parallel, a platinum salt hexahydrate $H_2PtCl_6.6H_2O$ (257.6 mg; 0.5 mmol, 1 eq.) is dissolved in 2 mL of milliQ water in a beaker. The solution is stirred well, until the solution is homogenous.

1.6 mL of the solution of metallic salt is added to the abovementioned reactor then it is stirred manually, until the mixture is limpid. This mixture has an orange yellow colour.

The resulting mixture is left to rest for a period of 15 minutes, so that it can stabilise.

Sodium borohydride (152 mg; 4 mmol; 15 eq.) is added to the mixture in a single time quickly and the mixture is immediately stirred vigorously (the sodium borohydride having to reduce the metal before the water). The mixture changes to an intense black colour.

The mixture is left at rest for a period from 1 to 2 hours, in such a way that the platinum is entirely reduced and that the $NaBH_4$ is entirely deactivated.

After two hours, the mixture is placed under ultrasounds for 5 minutes, stirring from time to time, in such a way that there is no longer any deposit at the bottom of the reactor.

Vulcan® XC 72 carbon black (finely ground beforehand) is added to the mixture, while the latter is still subjected to ultrasounds, the latter being maintained for 5 minutes, once the adding is carried out, while still maintaining a sporadic stirring. After 5 minutes, the reactor is strongly stirred manually then, after verification that the carbon black is not being deposited at the bottom of the reactor, the latter is again subjected to ultrasounds for 5 minutes before being, once again, manually stirred. This manipulation is reiterated, until the carbon is no longer deposited at the bottom of the reactor.

Then, once the carbon black is in suspension, the reactor is left in the ultrasound bath. Acetone (1 volume of acetone for one volume of microemulsion) is added little by little, by stirring manually at each phase of the adding. The resulting mixture is left 5 to 10 minutes in the ultrasound bath after the end of the adding.

The particles are then isolated by ultrafiltration on a hydrophilic membrane made of polyvinylidene fluoride (PVDF) Durapore (0.22 µm; GVWP 04700) under vacuum. The platinum particles supported on the carbon material (the carbon black) are washed by filtration by cycles of 4*30 mL of acetone, 4*30 mL of ethanol and 4*30 mL of MilliQ water (with a stirring between each washing). The particles obtained are then placed for 2 hours in the oven at a temperature of 135° C., in order to remove the last traces of Brij® 30.

The output is quantitative.

The particles obtained are analysed via elemental analysis attesting to the presence of carbon (at a rate of 60%) and of platinum (at a rate of 40%), which demonstrates that the platinum particles are supported on the carbon material.

b) Synthesis of Particles in a Polyol Medium Via Microwaves

In a first step, a platinum salt hexahydrate having formula $H_2PtCl_6.6H_2O$ (257 mg) is dissolved in 100 mL of ethylene glycol. The pH is then approximately 0.8. It is adjusted to 11 by adding a solution of soda.

Vulcan® XC 72 carbon black (finely ground beforehand) (0.145 mg) is then added to the solution obtained beforehand and the resulting mixture is placed under ultrasounds, until complete dispersion of the carbon black.

The mixture is heated by microwave radiation in a MARSXPress microwave oven from CEM® under an inert nitrogen atmosphere (Rise in temperature from 20° C. to 100° C. at atmospheric pressure and at a power of 1,600 W; Maintaining for 5 minutes at 100° C. at 1,600 W; Pulse: 80%).

The pH obtained at the end of the synthesis is equal to 11 at a temperature of 18° C. The pH is adjusted to 2 by adding a solution of hydrochloric acid, then 50 mL of milliQ water are added in order to homogenise the mixture. The resulting mixture is then placed under ultrasound for 5 minutes.

The particles are then isolated via ultrafiltration then rinsed abundantly with milliQ water and finally dried at 60° C. in the oven before being placed at 200° C. for 2 hours in the oven.

Example 4

This example shows the preparation of platinum particles prepared according to the modes of preparing of the example 3 grafted with the polymer prepared in the example 2, with these particles being as such grafted with grafts having the following formula:

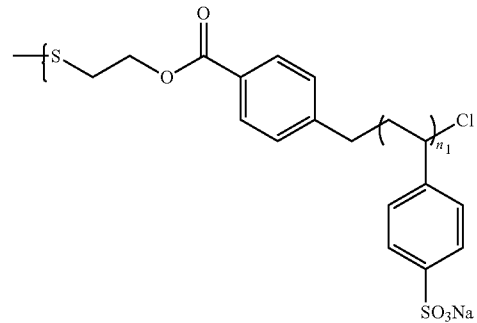

$n_1$ indicating the repetition number of the unit taken in parentheses.

Whether for the particles prepared according to the method 3a) or particles prepared according to the method 3b), the preparation protocol is as follows.

The particles prepared in the example 3 and hexylamine are introduced into a 25 mL flask. The flask is placed 15 minutes in an ultrasound bath, so that the suspension of particles is homogeneous. The polymer obtained in the example 2 is put into in a water/hexylamine mixture (50/50 by volume) then is introduced into the flask. The whole is placed under magnetic stirring for 12 hours.

The functionalised platinum particles are isolated by ultrafiltration then are subjected to various steps starting with a precipitation in acetone then subjected to various steps of washing (3*30 mL of acetone, 3*30 mL of ethanol and 3*30 mL of water).

These washing steps make it possible to remove the traces of polymers that may not have been grafted on the particles.

The particles are then placed for one night in the oven at 65° C. The table hereinbelow groups together the results of the various tests conducted according to the particulars of the protocol disclosed hereinabove.

| Test | Molar weight of the polymer (g) | Quantity of polymer engaged (in mg) | Quantity of particles engaged* (in mg) | Theoretical polymer weight ratio (in %) | Experimental polymer weight ratio* (in %) | Number of moles of polymer/g of particles |
|---|---|---|---|---|---|---|
| 1 (Method 3b) | 76,000 | 1.7 | 100 | 1.69 | 1.69 | $5.6*10^{-7}$ |
| 2 (Method 3b) | 140,000 | 3.1 | 100 | 3.05 | 3.05 | $5.6*10^{-7}$ |
| 3 (Method 3b) | 222,000 | 5.0 | 100 | 4.76 | 4.76 | $5.6*10^{-7}$ |
| 4 (Method 3b) | 300,000 | 6.8 | 100 | 6.33 | 6.33 | $5.6*10^{-7}$ |
| 5 (Method 3b) | 359,000 | 2.8 | 100 | 2.75 | 2.75 | $2.0*10^{-7}$ |
| 6 (Method 3b) | 359,000 | 4.0 | 100 | 3.89 | 3.88 | $2.8*10^{-7}$ |
| 7 (Method 3b) | 359,000 | 8.1 | 100 | 7.48 | 7.48 | $5.6*10^{-7}$ |
| 8 (Method 3b) | 359,000 | 16.2 | 100 | 13.92 | 13.92 | $1.1*10^{-6}$ |
| 9 (Method 3b) | 359,000 | 24.3 | 100 | 19.52 | 19.52 | $1.7*10^{-6}$ |
| 10 (Method 3b) | 359,000 | 32.3 | 100 | 24.44 | 24.43 | $2.3*10^{-6}$ |
| 11 (Method 3a) | 0 | 0 | 100 | 0 | 0 | 0 |
| 12 (Method 3b) | 0 | 0 | 100 | 0 | 0 | 0 |
| 13 (Method 3a) | 140,000 | 3.1 | 100 | 3.05 | 3.05 | $5.6*10^{-7}$ |

*measured by elemental analysis

In this table, it can be observed that there is a major difference in the active surface area between the particles obtained by the method 3a) (namely, the method involving a "water-in-oil" microemulsion) and the particles obtained by the method 3b (namely, the method involving a polyol and a heating via microwaves).

Indeed, this results in that the particles obtained by the method 3b have an active surface area approximately 2.5 times greater than the particles obtained by the method 3a.

For information, the active surface area is determined by cyclic voltammetry with a linear variation in the potential in the support medium ($HClO_4$ 0.1 M, deaerated by an inert gas)

In addition, it can be considered that the particles obtained by the method 3b have a better activity ($j_k$) with regards to the oxygen reduction reaction. For information, the catalytic activity of the catalyst is determined from the Koutecky-Levich method applied to the measurements of the polarisation curves carried out using an electrode with a rotating disc. The rotating disc makes it possible to record the reduction of oxygen in the liquid electrolyte at different rotating speeds of the electrode.

The characterisations are carried out in the following conditions:
- rotating speeds of the electrode: 2,500, 2,000, 1,500, 1,000 and 500 $rpm^{-1}$;
- speed of linear variation in potential set to 1 mV/s;
- HClO4 0.1 M medium saturated with oxygen.

b) Test in Cells

To do this, cells were carried out (respectively Cell 1 and Cell 2) with each one comprising an electrode-membrane-electrode assembly each comprising:
- an anode of the gas diffusion electrode type comprising 0.2 mg/cm$^2$ of commercial particles of platinum bonded to a carbon material (with these particles not being grafted);

Example 5

In this example, particles obtained in the example 4 are subjected to electrochemical analyses and tests in cells.

a) Electrochemical Characterisation of Particles

The electrochemical properties (accessible surface area, activity and selectivity) of the catalysts are important factors in the choice of the material to be used in the active cathode layers of fuel cells of the PEMFC type.

The presence of an organic crown could substantially modify its catalytic properties, which are, in theory, strongly linked to the surface condition of the catalyst.

The results of the electrochemical analyses (active surface area and catalytic activity) for particles obtained according to the two methods for synthesising nanoparticles are summarised in the table hereinbelow.

| Particles | Active surface area (in m$^2$/g) | Activity ($j_k$) (0.9 V) (in mA/cm$^2$) |
|---|---|---|
| Test 11 | 30 | 2.29 |
| Test 12 | 80 | 4.59 |
| Test 13 | 22 | 2.90 |
| Test 2 | 67 | 4.03 | a cathode of the gas diffusion electrode type comprising 0.4 mg/cm² of platinum particles obtained by one of the tests of the example 4;

a Nafion® NRE 211 membrane arranged between the anode and the cathode.

For the Cell 1, the cathode comprises platinum particles obtained in the test 2 of the example 4.

For the Cell 2, the cathode comprises platinum particles obtained in the test 13 of the example 4.

The electrode-membrane-electrode assemblies are carried out according to the following operating protocol.

Whether for the anode or for the cathode, the latter are prepared by simple pouring of a catalytic ink comprising the platinum particles concerned into an ethanol/water mixture (3:1) on a Sigracet ° 24BC gas diffusion layer (GDL).

Before being placed in the assembly, the Nafion® membrane is treated beforehand by hot pressing by pressing a reinforcement on either side of the latter at a temperature of 110° C. and at a pressure of 3 MPa pendant 90 seconds.

Finally, the gas diffusion electrodes (anode and cathode) are pressed on either side of the Nafion® membrane treated beforehand as such at a temperature of 115° C. and at a pressure of 3.5 MPa for 150 seconds.

The tests are conducted in a single cell of 5 cm² under $H_2/O_2$ (stoichiometry $\lambda_{O2}$=1.5 and $\lambda_{H2}$=1.5) under a pressure of 2 bars, at 60° C. and at 21% humidity.

Figure 1:
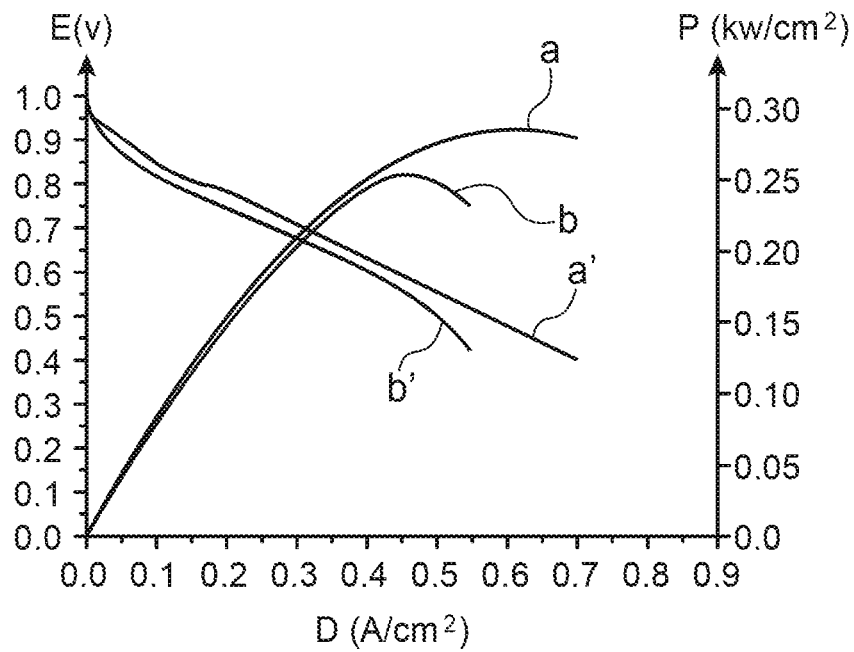

Curves showing the change in voltage E (in V) according to the current density (in A/cm²) are shown in FIG. 1 (curve a' for the Cell 1 and curve b' for the Cell 2) as well as the power curves (curve a for the Cell 1 and curve b for the Cell 2).

The tests in cells demonstrate that the catalyst prepared by the method for synthesising polyol via microwaves has better activity. This difference in activity can be observed in the activation zone corresponding to the low current densities, i.e. a current density between 0 and 0.1 A/cm². Indeed, in this zone, the curve a' has a slope much less steep than that of curve b', which shows the better catalytic activity and as such a better starting of the reactions on the fuel cell leading to a lesser drop in voltage.

Also note that the catalyst prepared by the method of synthesising polyol via microwaves is not as affected by the problems of the diffusion of reagents, which results in a curve a') which does not look like a curve corresponding to a flooding at high current densities, contrary to curve b'). This phenomenon of flooding can be explained by the substantial production of water which act as a barrier to the diffusion of reagents.

Example 6

In this example, the particles obtained in the tests 1, 2, 3, 4 and 7 of the example 4 were tested in order to determine their active surface area and their electrochemical activity with regards to the oxygen reduction reaction.

The results are listed in the table hereinbelow.

| Particles | Degree of polymerisation in number $DP_n$ | Number of moles of polymer/g of particles | Active surface area (in m²/g) | Activity ($j_k$) (0.9 V) (in mA/cm²) |
|---|---|---|---|---|
| Test 1 | 500 | 5.6*10⁻⁷ | 55 | 1.43 |
| Test 2 | 1,000 | 5.6*10⁻⁷ | 63 | 4.03 |
| Test 3 | 1,500 | 5.6*10⁻⁷ | 69 | 3.53 |
| Test 4 | 2,000 | 5.6*10⁻⁷ | 73 | 3.74 |
| Test 7 | 2,500 | 5.6*10⁻⁷ | 86 | 4.16 |

These results show particularly interesting properties in terms of active surface area and of activity for the particles obtained by the method of polyol synthesis via microwaves and, in particular, those grafted with polymers with a high molecular weight.

Example 7

In this example, the particles obtained in the tests 2, 3, 4 and 7 of the example 4 were tested in cells in the same assembly and test conditions as those specified in the example 5 hereinabove.

Figure 2:
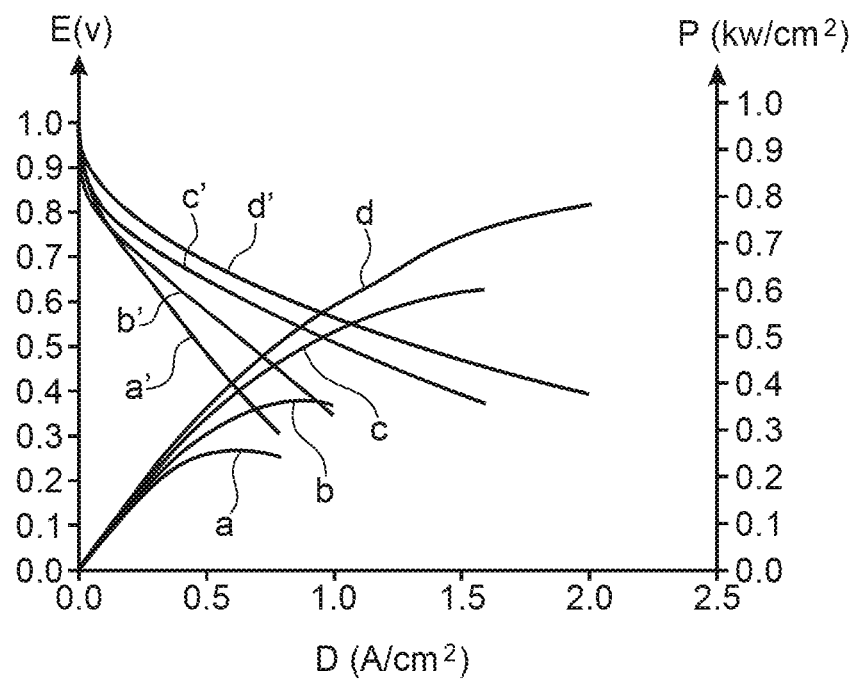

The results are listed in FIG. 2 provided in the appendix, which shows, on the one hand, the polarisation curves showing the change in the voltage E (in V) according to the current density D (in A/cm²) (respectively curves a'), b'), c') and d') for cells comprising particles of tests 2, 3, 4 and 7) and the power curves showing the change in the power density P (in kW/cm²) according to the current density D (in A/cm²) (respectively curves a), b), c) and d) for cells comprising particles of tests 2, 3, 4 and 7).

Particularly interesting results are observed with the particles obtained by the method of synthesising polyol via microwaves and, in particular, those grafted with polymers with a high molecular weight and with grafting rates of 5.6*10-7.

Example 8

In this example, the particles obtained in the tests 12, 5, 6, 7, 8, 9 and 10 of the example 4 were tested in order to determine their active surface area and their electrochemical activity with regards to the oxygen reduction reaction.

The results are listed in the table hereinbelow.

| Particles | Degree of polymerisation in number $DP_n$ | Number of moles of polymer/g of particles | Active surface area (in m²/g) | Activity ($j_k$) (0.9 V) (in mA/cm²) |
|---|---|---|---|---|
| Test 12 | — | — | 80 | 4.59 |
| Test 5 | 2,500 | 2.0*10⁻⁷ | 89 | 3.86 |
| Test 6 | 2,500 | 2.8*10⁻⁷ | 98 | 8.63 |
| Test 7 | 2,500 | 5.6*10⁻⁷ | 86 | 4.16 |
| Test 8 | 2,500 | 1.1*10⁻⁶ | 83 | 2.93 |
| Test 9 | 2,500 | 1.7*10⁻⁶ | 73 | 1.34 |
| Test 10 | 2,500 | 2.3*10⁻⁶ | 68 | 1.31 |

These results show particularly interesting properties in terms of active surface area and of activity for the particles obtained by the method of synthesising polyol by microwaves and, in particular, those with intermediate grafting rates.

Surprisingly, the maximum active surface areas obtained are obtained with grafted particles (cf. test 6, namely the test where the particles are grafted with a polymer comprising a molecular weight of 359,000 g/mol and a grafting mass rate of 3.88%) comparatively to the non-grafted particles (cf. test 12), with a gain in the active surface area of 19%. Concerning the electrochemical activity with regards to the reduction of oxygen ($j_k$), the latter is 8.63 mA/cm² for the grafted particles of the test 6 compared to 4.59 mA/cm² for the non-grafted particles of the test 12, which represents an increase of 88%.

This contributes in demonstrating that the grafting of polymer not only does not reduce the accessibility of the platinum surface but, on the contrary, compounds the latter.

Example 9

In this example, the particles obtained in the tests 6, 7, 8 and 9 of the example 4 were tested in cells in the same assembly and test conditions as those specified in the example 5 hereinabove.

The results are listed in FIG. 3 provided in the appendix, which shows, on the one hand, the polarisation curves showing the change in the voltage E (in V) according to the current density D (in A/cm$^2$) (respectively curves a'), b'), c') and d') for cells comprising particles of tests 6, 7, 8 and 9) and the power curves representing the change in the power density P (in kW/cm$^2$) according to the current density D (in A/cm$^2$) (respectively curves a), b), c) and d) for cells comprising particles of tests 6, 7, 8 and 9).

Particularly interesting results are observed with the particles obtained by the method of synthesising polyol via microwaves and, in particular, those grafted with polymers of high molecular weight and with relatively low grafting rates.

The maximum power obtained with the particles with the best performance is nearly 400% higher than in the case of the particles obtained by the water-in-oil synthesis. Indeed, by referring to curve a) (obtained with particles of the test 6), the maximum power density obtained is approximately 1 kW/cm$^2$, while the maximum power density obtained is approximately 0.25 kW/cm$^2$ (obtained with the particles of the test 13, as shown on curve b of FIG. 1).

What is claimed is:

1. Method for preparing platinum particles bonded to a carbon material, said particles being grafted with grafts consisting of at least one polymer comprising at least one styrene repeating unit having at least one proton-conducting group, said method comprising:

a) a step of preparing said platinum particles bonded to a carbon material comprising an operation of heating under microwaves of a mixture comprising a platinum salt, said carbon material and at least one polyol compound, subject to which said particles are obtained;

b) a step of preparing at least one ethylene polymer by ATRP polymerisation of an ethylene monomer with an ATRP initiator having the following formula (I):

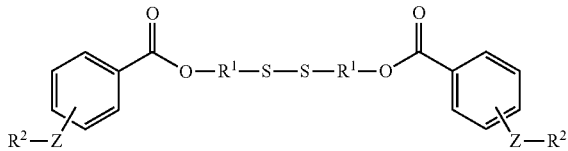

(I)

wherein:
   the R$^1$ groups represent, independently of one another, an organic spacer group;
   the Z groups represent, independently of one another, a single bond or an organic spacer group;
   the R$^2$ groups represent, independently of one another, a halogen atom;

the resulting polymer having the following formula (II):

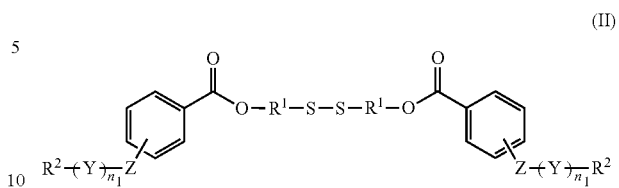

(II)

wherein Y corresponds to the styrene repeating unit having at least one proton-conducting group and n$_1$ to the repetition number of the repeating unit taken in parentheses, the R$^1$, R$^2$ and Z being such as defined hereinabove;

c) a step of contacting particles obtained in a) with the polymer obtained in b), subject to which particles are obtained grafted with grafts having the following formula (III):

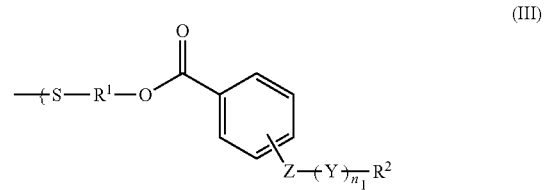

(III)

the brace indicating the location where the grafts are bonded, covalently, to the particles and the R$^1$, R$^2$, Z, Y and n$_1$ being such as defined hereinabove.

2. Method according to claim 1, wherein the platinum salt is a platinum halide salt.

3. Method according to claim 1, wherein the carbon material is graphite, carbon black, carbon fibres, carbon tubes or graphene.

4. Method as claimed in claim 1, wherein the carbon material is carbon black.

5. Method as claimed in claim 1, wherein the polyol compound is a hydrocarbon compound comprising at least two carbon atoms each having at least one —OH group.

6. Method as claimed in claim 1, wherein the polyol compound is ethylene glycol.

7. Method as claimed in claim 1, wherein the step a) is carried out at a basic pH.

8. Method as claimed in claim 1, wherein R$^1$ and Z represent, independently of one another, an alkylene group.

9. Method as claimed in claim 1, wherein the —Z—R$^2$ groups are located in para position with respect to the —COO— groups.

10. Method as claimed in claim 1, wherein the ATRP initiator is a compound having the following formula (IV):

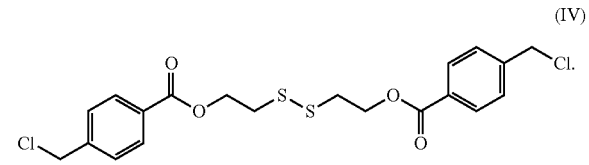 [SMILES: O=C(OCCSSCCOC(=O)c1ccc(CCl)cc1)c1ccc(CCl)cc1]

(IV)

11. Method as claimed in claim 1, wherein the proton-conducting group is a sulphonic acid group —SO$_3$H, a carboxylic acid group —CO$_2$H or a phosphonic acid group —PO$_3$H$_2$, these groups being able to be present optionally in the form of salts.

12. Method as claimed in claim 1, wherein the styrene monomer is a monomer having the following formula (V):

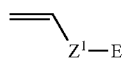
(V)

wherein:
Z$^1$ corresponds to a phenylene group; and
E corresponds to a proton-conducting group, optionally in the form of a salt.

13. Method as claimed in claim 1, wherein the styrene monomer is a sodium styrene sulphonate monomer.

14. Platinum particles being able to be obtained by a method according to claim 1, said platinum particles being bonded to a carbon material and being grafted with grafts having the following formula (III):

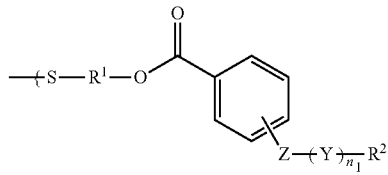
(III)

wherein R$^1$, R$^2$, Z, Y and n$_1$ have the same meaning as those given in claim 1.

15. Particles according to claim 14, wherein Y is a repeating unit coming from the repetition of a sodium styrene sulphonate monomer.

16. Electrode comprising particles such as defined according to claim 14.

17. Fuel cell comprising at least one electrode-membrane-electrode assembly, wherein at least one of its electrodes is an electrode such as defined in claim 16.

* * * * *

UNITED STATES PATENT AND TRADEMARK OFFICE
CERTIFICATE OF CORRECTION

PATENT NO. : 10,673,076 B2  
APPLICATION NO. : 16/089240  
DATED : June 2, 2020  
INVENTOR(S) : Pierrick Buvat et al.

Page 1 of 1

It is certified that error appears in the above-identified patent and that said Letters Patent is hereby corrected as shown below:

On the Title Page

Item (73) Assignee, "COMMISSARIAT À L'ÉNERGIE ATOMOIQUE ET AUX ÉNERGIES ALTERNATIVES" should be --COMMISSARIAT À L'ÉNERGIE ATOMIQUE ET AUX ÉNERGIES ALTERNATIVES--

In the Specification

Column 4, Line 50, "and the Fe, $R^2$, Z, Y and" should be --and the $R^1$, $R^2$, Z, Y and--

Signed and Sealed this  
Ninth Day of November, 2021

Drew Hirshfeld  
*Performing the Functions and Duties of the*  
*Under Secretary of Commerce for Intellectual Property and*  
*Director of the United States Patent and Trademark Office*